United States Patent
McGuinness et al.

(10) Patent No.: US 10,272,428 B2
(45) Date of Patent: Apr. 30, 2019

(54) MICROFLUIDIC SENSING DEVICE AND SYSTEM

(71) Applicant: Hewlett-Packard Development Company, L.P., Houston, TX (US)

(72) Inventors: Nicholas M. McGuinness, San Diego, CA (US); Manish Giri, Corvallis, OR (US); Melinda M. Valencia, San Diego, CA (US); Chantelle Domingue, Corvallis, OR (US); Andrew L. Van Brocklin, Corvallis, OR (US); Dustin W. Blair, Escondido, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 14/787,230

(22) PCT Filed: Apr. 30, 2013

(86) PCT No.: PCT/US2013/038725
§ 371 (c)(1),
(2) Date: Oct. 26, 2015

(87) PCT Pub. No.: WO2014/178827
PCT Pub. Date: Nov. 6, 2014

(65) Prior Publication Data
US 2016/0114319 A1  Apr. 28, 2016

(51) Int. Cl.
*B01L 3/00* (2006.01)
*G01N 15/06* (2006.01)
(Continued)

(52) U.S. Cl.
CPC ..... *B01L 3/50273* (2013.01); *B01L 3/502715* (2013.01); *B01L 3/502753* (2013.01);
(Continued)

(58) Field of Classification Search
CPC .......... B01L 3/00; G01N 15/06; G01N 33/00; G01N 33/48
(Continued)

(56) References Cited

U.S. PATENT DOCUMENTS 7,744,738 B1 * 6/2010 Gagnon et al. ............... 204/643
8,895,311 B1 * 11/2014 Handique et al. ............. 436/43
(Continued)

FOREIGN PATENT DOCUMENTS

CN  1460855  12/2003
CN  201041563  3/2008
(Continued)

OTHER PUBLICATIONS

Berney, H. et al., "Impedance Measurement Monitors Blood Coagulation", Analog Dialogue, Aug. 2008, vol. 42, No. 3.
(Continued)

*Primary Examiner* — Brian J. Sines
(74) *Attorney, Agent, or Firm* — HP Inc. Patent Department (57) ABSTRACT

A microfluidic device can include: a channel; a fluid inlet to pass fluid into the channel from a reservoir; a sensor disposed in the channel; and a pump actuator disposed in the channel apart from the sensor to induce fluid flow into the channel.

5 Claims, 5 Drawing Sheets

(51) Int. Cl.
*G01N 33/00* (2006.01)
*G01N 33/48* (2006.01)
*G01N 15/10* (2006.01)

(52) U.S. Cl.
CPC ...... *G01N 15/1031* (2013.01); *B01L 2200/10* (2013.01); *B01L 2300/024* (2013.01); *B01L 2300/0636* (2013.01); *B01L 2300/0645* (2013.01); *B01L 2300/0681* (2013.01); *B01L 2400/0487* (2013.01); *G01N 2015/1006* (2013.01)

(58) Field of Classification Search
USPC ........... 422/68.1, 502, 503, 504, 505, 82.01, 422/82.02; 436/43, 149, 150
See application file for complete search history.

(56) References Cited

U.S. PATENT DOCUMENTS

| | | | |
|---|---|---|---|
| 2002/0079219 A1* | 6/2002 | Zhao et al. | 204/451 |
| 2002/0122747 A1* | 9/2002 | Zhao et al. | 422/99 |
| 2004/0072278 A1* | 4/2004 | Chou et al. | 435/29 |
| 2005/0092662 A1* | 5/2005 | Gilbert | B01L 3/502707 210/97 |
| 2005/0230251 A1* | 10/2005 | Eidsnes et al. | 204/450 |
| 2007/0003434 A1 | 1/2007 | Padmanabhan et al. | |
| 2008/0085219 A1 | 4/2008 | Beebe et al. | |
| 2010/0075340 A1* | 3/2010 | Javanmard | B01D 15/3804 435/7.1 |
| 2012/0007921 A1* | 1/2012 | Govyadinov | B41J 2/1404 347/54 |
| 2012/0084022 A1 | 4/2012 | Giovangrandi et al. | |
| 2012/0149021 A1* | 6/2012 | Yung et al. | 435/6.12 |
| 2013/0016335 A1 | 1/2013 | Lo et al. | |
| 2013/0155135 A1* | 6/2013 | Govyadinov | B41J 2/14129 347/10 |
| 2013/0248369 A1* | 9/2013 | Dekleva | B01L 3/502715 204/603 |
| 2013/0313116 A1* | 11/2013 | Palmer | B81B 1/00 204/604 |
| 2016/0114319 A1 | 4/2016 | McGuinness et al. | |

FOREIGN PATENT DOCUMENTS

| | | |
|---|---|---|
| CN | 101576557 | 11/2009 |
| CN | 101643701 | 2/2010 |
| CN | 101650370 | 2/2010 |
| CN | 102985261 | 3/2013 |
| EP | 2259044 A1 | 12/2010 |
| EP | 2992327 | 9/2016 |
| JP | H05-240872 | 9/1993 |
| JP | 2002-233792 | 8/2002 |
| JP | 2003-057223 | 2/2003 |
| JP | 2003-240757 | 8/2003 |
| JP | 2005-537923 | 12/2005 |
| JP | 2006-071388 | 3/2006 |
| JP | 2006-180810 | 7/2006 |
| JP | 2007-526762 | 9/2007 |
| JP | 2008-522793 | 7/2008 |
| JP | 2008-529033 | 7/2008 |
| JP | 2008-261832 | 10/2008 |
| JP | 2009-115731 | 5/2009 |
| JP | 2010-068783 | 4/2010 |
| JP | 2010-203779 | 9/2010 |
| JP | 2011-122858 | 6/2011 |
| JP | 2011203272 | 10/2011 |
| JP | 2011209036 | 10/2011 |
| JP | 2012-042424 | 3/2012 |
| JP | 2012-523571 | 10/2012 |
| KR | 20110056497 | 5/2011 |
| KR | 20120080842 | 7/2012 |
| WO | WO-2010/018833 | 2/2010 |
| WO | WO-2010111605 | 9/2010 |
| WO | WO-2011/067961 | 6/2011 |
| WO | WO-2011/137039 | 11/2011 |
| WO | WO-2011146149 | 11/2011 |
| WO | WO-2012003348 | 1/2012 |
| WO | WO-2012031630 | 3/2012 |

OTHER PUBLICATIONS

International Search Report, Korean Intellectual Property Office, dated Jan. 21, 2014, PCT Patent Application No. PCT/US2013/038725, 3 pages.
Sabounchi, P. et al., "Sample Concentration and Impedance Detection on a Microfluidic Polymer Chip", Biomedical Microdevices, May 17, 2008, vol. 10, No. 3.
Zhu, H. et al., "Cost-Effective and Rapid Blood Analysis on a Cell-Phone", Dec. 22, 2012; Lab on a Chip. vol. 13, No. 7.
Shoji, Shuichi, "Trend and Future of Micro Total Analysis Systems (µTAS)", Journal of the Japan Society for Precision Engineering, Japan, May 11, 1999, vol. 65, No. 5, p. 655-658.

* cited by examiner

MICROFLUIDIC SENSING DEVICE AND SYSTEM

CROSS-REFERENCE TO RELATED APPLICATION

This application is a U.S. National Stage Application of and claims priority to International Patent Application No. PCT/US2013/038725, filed on Apr. 30, 2013, and entitled "MICROFLUIDIC SENSING DEVICE AND SYSTEM," which is hereby incorporated by reference in its entirety.

BACKGROUND

Microfluidics is an increasingly important technology that applies across a variety of disciplines including engineering, physics, chemistry, microtechnology and biotechnology. Microfluidics involves the study of small volumes of fluid and how to manipulate, control and use such small volumes of fluid in various microfluidic systems and devices such as microfluidic chips. For example, microfluidic biochips (referred to as "lab-on-chip") are used in the field of molecular biology to integrate assay operations for purposes such as analyzing enzymes and DNA, detecting biochemical toxins and pathogens, diagnosing diseases, etc.

BRIEF DESCRIPTION OF THE DRAWINGS

Some embodiments of the invention are described with respect to the following figures.

DETAILED DESCRIPTION

Figure 1:
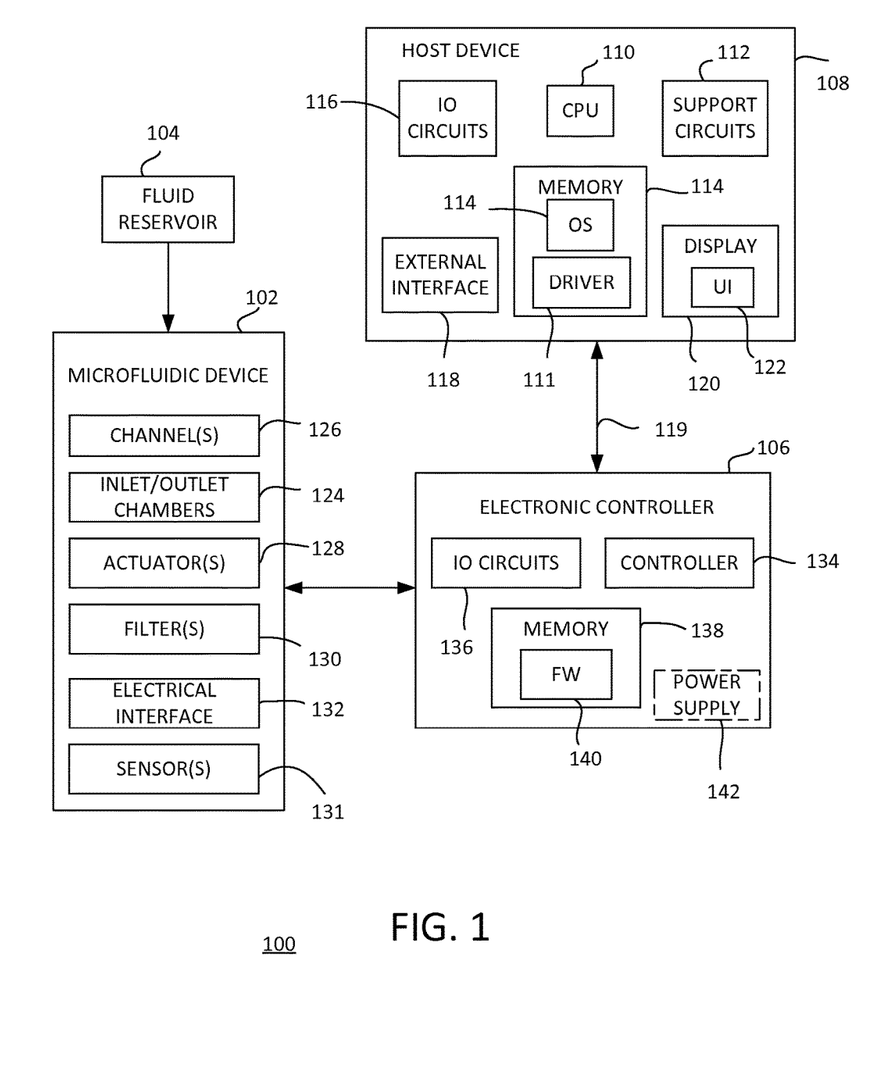
FIG. 1 shows a microfluidic diagnostic system according to an example implementation.

A living cell is the basic structural and functional unit of an organism. Most animal and plant cells range in size from 1-100 micrometers and contain vital health information. Cell-based diagnostics is the gold standard for detecting infection diseases (HIV, Malaria, Tuberculosis), as well as chronic diseases (cancer, cardiac diseases, autoimmune diseases). Traditional cellular-level diagnostic tools are expensive, require specialized training to operate, and cannot always be deployed at the point-of-care setting. The microfluidic diagnostic system described herein can be used to provide a configurable and mobile platform to address the worldwide need for affordable health diagnostics. In examples described herein, FIG. 1 shows a microfluidic diagnostic system 100 according to an example implementation. The example microfluidic diagnostic system 100 includes a microfluidic device 102, an external fluid reservoir 104, an electronic controller 106, and a host device 108. In general, fluid is placed in the fluid reservoir 104. The fluid can be a host fluid having particles (e.g., a blood sample, an ink containing pigments/particles, or the like). The fluid 102 is processed through microfluidics and applied to a sensor in the microfluidic device 102 under control of the electronic controller 106. The microfluidic device 102 provides an electrical output signal representing the sensor data to the electronic controller 106. The electronic controller 106 is under control of the host device 108. The host device 108 can send and receive data to and from the electronic controller 106, including command information for controlling the microfluidic device 102 and sensor data obtained from the microfluidic device 102.

The host device 108 generally includes a central processing unit (CPU) 110, various support circuits 112, memory 114, various input/output (IO) circuits 116, and an external interface 118. The CPU 110 can include any type of microprocessor known in the art. The support circuits 112 can include cache, power supplies, clock circuits, data registers, and the like. The memory 114 can include random access memory, read only memory, cache memory, magnetic read/write memory, or the like or any combination of such memory devices. The IO circuits 116 can cooperate with the external interface 118 to facilitate communication with the electronic controller 106 over a communication medium 119. The communication medium 119 can be any type of electrical, optical, radio frequency (RF), or the like transfer path.

In an example, the external interface 118 can include a universal serial bus (USB) controller capable of sending and receiving data to the electronic controller 106, as well as providing power to the electronic controller 106, over a USB cable. It is to be understood that other types of electrical, optical, or RF interfaces to the electronic controller 106 can be used to send and receive data and/or provide power.

The memory 114 can store an operating system (OS) 109 and a driver 111. The OS 109 and the driver 111 can include instructions executable by the CPU 110 for controlling the host device 108 and the electronic controller 106 through the external interface 118. The driver 111 provides an interface between the OS 109 and the electronic controller 106. Accordingly, the host device 108 comprises a programmable device that includes machine-readable instructions stored in the form of one or more software modules, for example, on non-transitory processor/computer readable-media (e.g., the memory 114).

The host device 108 can include a display 120 through which the OS 109 can provide a user interface (UI) 122. A user can use the UI 122 to interact with the OS 109 and the driver 111 to control the electronic controller 106, and display data received from the electronic controller 106. It is to be understood that the host device 108 can be any type of general or specific purposed computing device. In an example, the host device 108 can be a mobile computing device, such as a "smart phone," "tablet" or the like.

The external fluid reservoir 104 is in fluidic communication with the microfluidic device 102. The external fluid reservoir 104 is configured to hold and supply fluidic components/samples and/or solutions to the microfluidic device 102. The microfluidic device 102 can be implemented as a chip-based device. Various example implementations of the device 102 are described below and can generally include inlet/outlet chamber(s) 124, microfluidic channel(s) 126, actuator(s) 128, microfluidic filter(s) 130, sensor(s) 131, and an electrical interface 132. The electronic controller 108 is coupled to the electrical interface 132 for energizing the actuator(s) 128 and sensor(s) 131. In general, the structures and components of the chip-based microfluidic device 102 can be fabricated using conventional integrated circuit microfabrication techniques such as electroforming, laser ablation, anisotropic etching, sputtering, dry and wet etching, photolithography, casting, molding, stamping, machining, spin coating, laminating, and so on.

In one example, the electronic controller 108 includes a controller 134, 10 circuits 136, and a memory 138. The controller 134 can include any type of microcontroller or microprocessor known in the art. In an example, the electronic controller 108 receives power from the host device 108. In another example, the electronic controller 108 can include a power supply 142.

The memory 138 can store firmware 140, which can include instructions executable by the controller 134 for controlling the microfluidic device 102 and communicating with the host device 108. Accordingly, the electronic controller 106 comprises a programmable device that includes machine-readable instructions stored in the form of one or more software/firmware modules, for example, on non-transitory processor/computer readable-media (e.g., the memory 138). It is to be understood that, which described as a controller executing instructions from a firmware, the electronic controller 108 can be implemented using hardware, software/firmware, or a combination thereof. For example, all or a portion of the electronic controller 106 can be implemented using a programmable logic device (PLD, application specific integrated circuit (ASIC), or the like.

Figure 2:
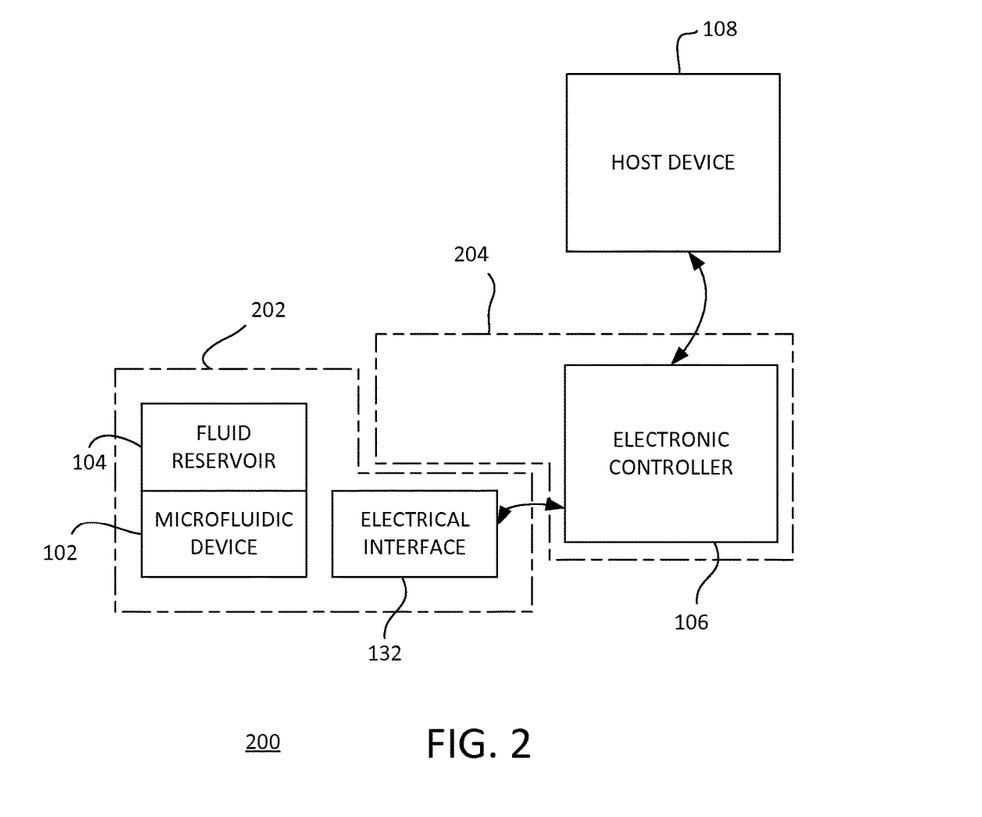
FIG. 2 is a block diagram showing an exemplary configuration of the diagnostic system shown in FIG. 1 according to an example implementation.

FIG. 2 is a block diagram showing an exemplary configuration 200 of the diagnostic system 100 shown in FIG. 1 according to an example implementation. In the example, the fluid reservoir 104, the microfluidic device, and the electrical interface 132 are part of a first module 202. The electronic controller 106 is part of a second module 204. The first module 202 can be mechanically coupled to the second module 204 such that the electronic controller 106 is electrically coupled to the electrical interface 132. The first module 202 is removably coupled to the second module 204 so that it can be coupled and uncoupled as needed. The electronic controller 106 can be coupled to the host device 108 as described above.

Figure 3:
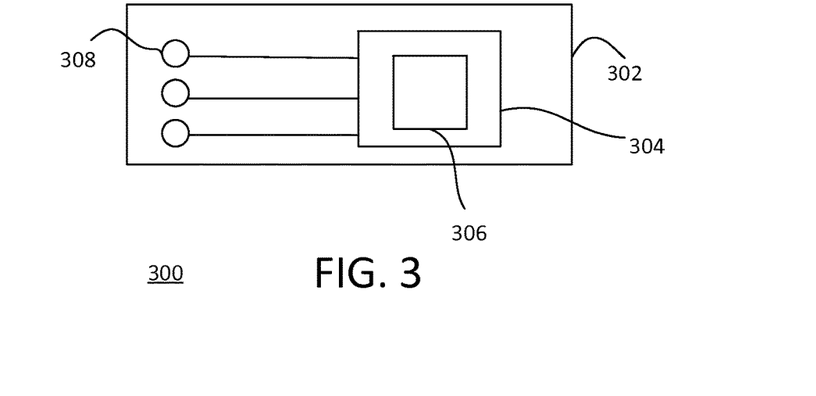
FIG. 3 is a block diagram showing a sensor module according to an example implementation.

FIG. 3 is a block diagram showing a sensor module 300 according to an example implementation. The sensor module 300 can be used as the module 202 in the diagnostic system 100 as shown in FIGS. 1 and 2. The sensor module 300 includes a substrate 302, a microfluidic structure 304, a fluid reservoir 306, and electrical interface 308. The electrical interface 308 transfers energy to active components in the microfluidic structure 304 via conductors 310 on the substrate 302. The fluid reservoir 306 is configured to hold and supply fluidic components/samples and/or solutions to the microfluidic structure 304. Example microfluidic structures are described below.

Figure 4:
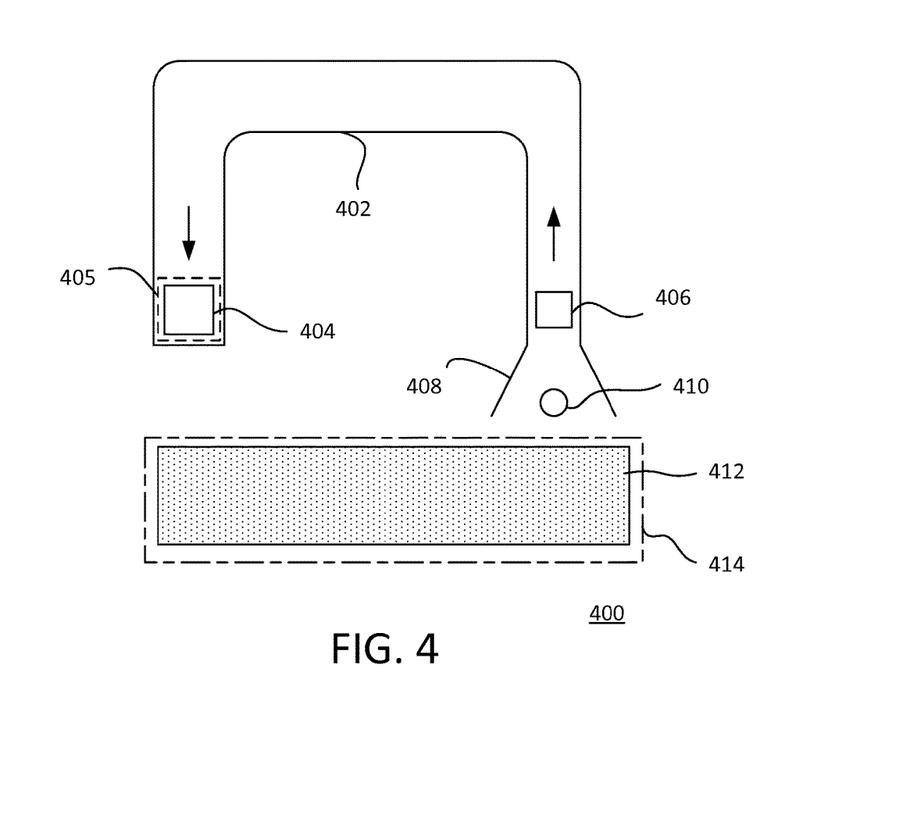
FIG. 4 is a schematic diagram of a microfluidic structure suitable for implementing a microfluidic sensor according to an example implementation.

FIG. 4 is a schematic diagram of a microfluidic structure 400 suitable for implementing a microfluidic sensor according to an example implementation. The microfluidic structure 400 includes a microfluidic channel 402, a pump actuator 404, a sensor 406, a nozzle 405 (e.g., outlet), and an inlet 408. A portion 414 of the fluid reservoir is shown. In an example, a mesh filter 412 can be provided in the fluid reservoir 414 for filtering particles in the applied fluid sample. While the shape of the fluid channel 402 is shown generally throughout this disclosure as "u-shaped", this is not intended as a limitation on the shape of the channel 402. Thus, the shape of the channel 402 can include other shapes, such as curved shapes, snake-like shapes, shapes with corners, combinations thereof, and so on. Moreover, the channel 402 is not shown to any particular scale or proportion. The width of the channel 402 as fabricated on a device can vary from any scale or proportion shown in the drawings of this disclosure. The arrows in the channel indicate and example direction of fluid flow through the channel.

The inlet 408 provides an opening for the channel 402 to receive the fluid. The filter 410 is disposed in the inlet 408. The filter 410 prevents particles in the fluid of a particular size (depending on the size of the filter 410) from entering the channel 402. The inlet 408 can have a larger width and volume than the channel 402.

In an example, the sensor 406 is disposed in the channel 402 near the inlet 408 (e.g., closer to the inlet 408 than the pump actuator 404). In another example, the sensor 406 can be disposed in the inlet 408. The sensor 406 can be an impedance sensor formed using known semiconductor techniques. The sensor 406 can detect impedance changes as particles in the fluid pass over the sensor 406.

The pump actuator 404 is disposed near a closed end of the channel 402 downstream from the sensor 406. The pump actuator 404 can be a fluidic inertial pump actuator, which can be implemented using a wide variety of structures. For example, the pump actuator 404 can be a thermal resistor that produces vapor bubbles to create fluid displacement within the channel 402. The displaced fluid can be ejected from the nozzle 405. Actuators can also be implemented as piezo elements (e.g., PZT) whose electrically induced deflections generate fluid displacements within the channel 402. Other deflective membrane elements activated by electrical, magnetic, and other forces are also possible for use in implementing the pump actuator 404.

Figure 5:
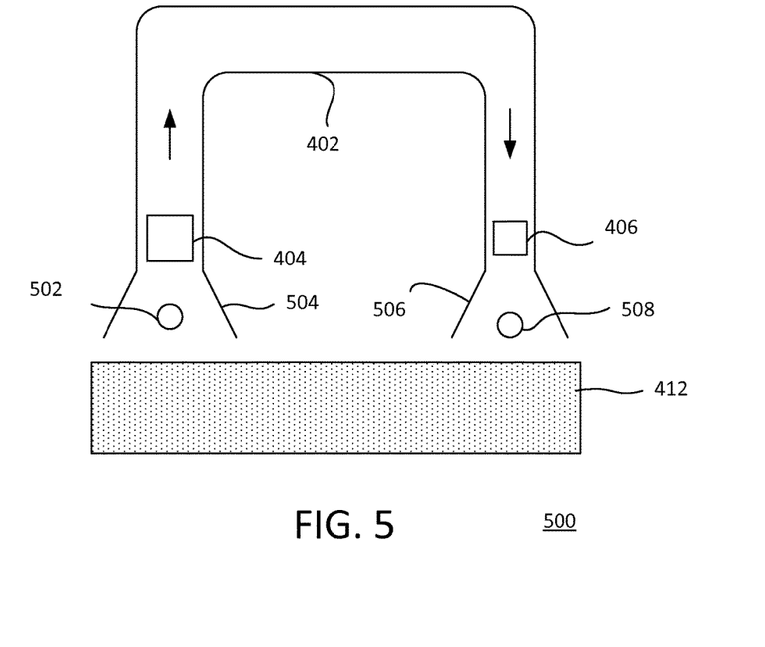
FIG. 5 is a schematic diagram of a microfluidic structure suitable for implementing a microfluidic sensor according to an example implementation.

FIG. 5 is a schematic diagram of a microfluidic structure 500 suitable for implementing a microfluidic sensor according to an example implementation. Elements of FIG. 5 that are the same or similar to those of FIG. 4 are described in detail above. In the example of FIG. 4, flow fluid is induced by ejection using the pump actuator 404. In the present example of FIG. 5, fluid flow is induced by recirculation using the pump actuator 404. The channel 402 includes an inlet 504 at the end of the channel 402 opposite an outlet 506. A filter 502 can be formed in the inlet 504, and a filter 508 can be disposed in the outlet 506, to filter particles of a desired size (based on filter size). The arrows denote direction of fluid flow in the channel 402. Instead of ejecting the fluid, the channel 402 recirculates the fluid back to the reservoir.

Figure 6:
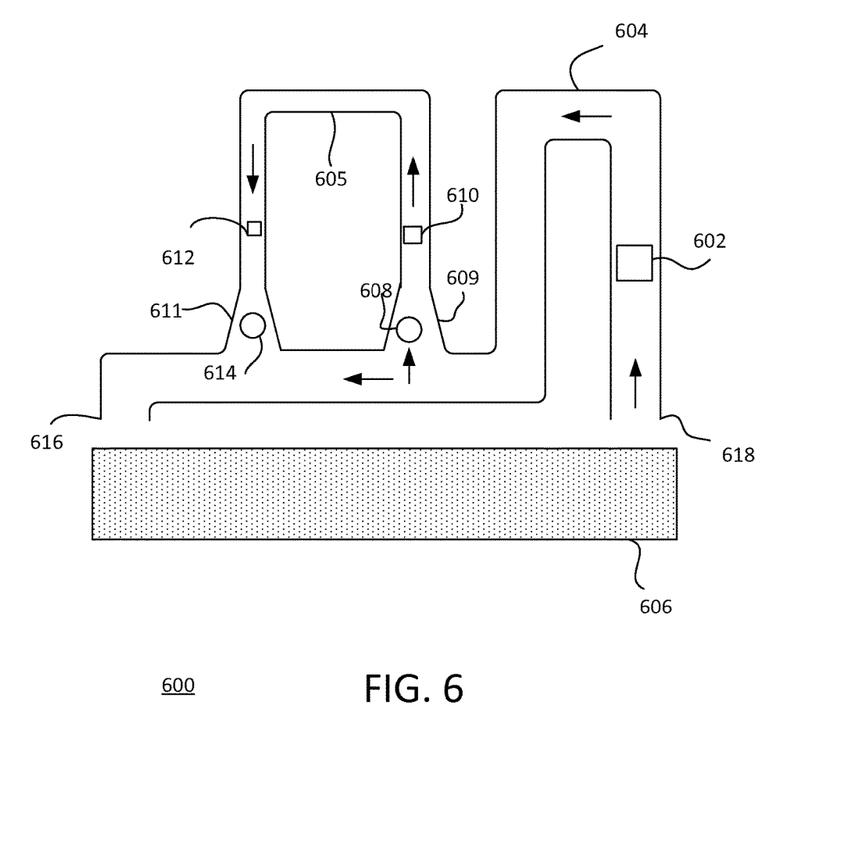
FIG. 6 is a schematic diagram of a microfluidic structure suitable for implementing a microfluidic sensor according to an example implementation.

FIG. 6 is a schematic diagram of a microfluidic structure 600 suitable for implementing a microfluidic sensor according to an example implementation. The example of FIG. 6 shows a cross-flow structure that can separate particles of different sizes within the channel. In this example, the structure 600 includes a primary channel 604 and a secondary channel 605. Arrows show an example direction of fluid flow from an inlet 618 to an outlet 616. Note this fluid flow direction is an example, and that the fluid can flow in the reverse direction. Fluid can enter the primary channel 604 from the reservoir through an optional mesh filter 606. Further, although omitted for clarity, filters can be disposed within the inlet 618 and/or outlet 616 as described in the structures above. A pump actuator 602 is disposed in the primary channel 604 near the inlet 618. The secondary channel 605 includes an inlet 609 and an outlet 611. Filters 608 and 614 can be disposed in the inlet 609 and outlet 611, respectively. A sensor 610 is disposed in the secondary channel 605 near the inlet 609. A pump actuator 612 is disposed in the secondary channel 605.

Fluid flows into the primary channel 604 from the inlet 618. The pump actuator 602 induces fluid flow into the primary channel 604. At the inlet 609 of the secondary channel 605, fluid can flow to the secondary channel 605 and continue along the primary channel 604. The filter 608 and the filter 614 can be designed such that smaller particles flow into the secondary channel 605 than in the primary channel 604. The smaller particles rejoin the fluid in the primary channel 604 at the outlet 611. The pump actuator 612 induces fluid flow into the secondary channel 605. The sensor 610 can measure the particles in the secondary channel 605 (e.g., impedance sensing).

By way of example, the microfluidic structure 600 has been shown and described as having two channels (primary and secondary). It is to be understood that the microfluidic structure can have any number of channels. For example, a microfluidic structure can include two different secondary loops fluidically coupled to a primary loop. In another example, a microfluidic structure can include one loop, coupled to another loop, coupled to another loop, and so on. Various configurations of a microfluidic device can be devised having any number of channels or loops.

In the foregoing description, numerous details are set forth to provide an understanding of the present invention. However, it will be understood by those skilled in the art that the present invention may be practiced without these details. While the invention has been disclosed with respect to a limited number of embodiments, those skilled in the art will appreciate numerous modifications and variations therefrom. It is intended that the appended claims cover such modifications and variations as fall within the true spirit and scope of the invention.

What is claimed is:

1. A diagnostic sensor system, comprising:
   a host device comprising a processing unit, a user interface and an external interface:
   a sensor module having a fluid reservoir, a microfluidic device external to the fluid reservoir, and an electrical interface, the microfluidic device being in fluidic communication with the fluid reservoir and electrical communication with the electrical interface, wherein the microfluidic device includes a channel having an inlet and an outlet both in fluidic communication with the reservoir, a sensor disposed near the inlet or near the outlet, and a pump actuator disposed away from the sensor in the channel configured to induce fluid flow into the channel over the sensor; and
   an electronic controller module configured to be detachably coupled to the sensor module, the electronic controller module including an electronic controller in electrical communication with the microfluidic device through the electrical interface, wherein the sensor module is configured to be mechanically uncoupled and electrically uncoupled from the electronic controller module and detachably coupled to the host module, wherein the electronic controller is in electrical communication with the processing unit of the host device through the external interface, wherein the host device is configured to be mechanically uncoupled and electrically uncoupled from the electronic controller module.

2. The diagnostic sensor system of claim 1, wherein the microfluidic device includes an impedance sensor disposed in the channel.

3. The diagnostic sensor system of claim 2, wherein the channel includes a primary channel and a secondary channel, the secondary channel in fluidic communication with the primary channel.

4. The diagnostic sensor system of claim 1, wherein the pump actuator is configured to induce fluid flow from the fluid reservoir into the channel, over the sensor when the sensor module is mechanically coupled and electrically coupled to the electronic controller module and the electrical interface receives electrical energy from the electronic controller module.

5. The diagnostic sensor system of claim 1, wherein the sensor module further comprises:
   a primary channel;
   a second inlet to pass fluid into the primary channel from the fluid reservoir;
   a second pump actuator disposed in the primary channel configured to induce fluid flow from the second inlet into the primary channel;
   wherein the inlet of the channel and the outlet of the channel are in fluidic communication with the primary channel downstream from the second pump actuator,
   wherein the channel is branched from the primary channel at the inlet and connected to the primary channel at the outlet, which is located downstream from the inlet along the primary channel, and
   wherein the second pump actuator is configured to induce fluid flow such that part of the fluid flowing through the primary channel flows into the channel at the inlet, continues along the channel to the outlet, and joins a fluid flowing through the primary channel at the outlet.

* * * * *

UNITED STATES PATENT AND TRADEMARK OFFICE
CERTIFICATE OF CORRECTION

PATENT NO. : 10,272,428 B2
APPLICATION NO. : 14/787230
DATED : April 30, 2019
INVENTOR(S) : Nicholas M. McGuinness et al.

Page 1 of 1

It is certified that error appears in the above-identified patent and that said Letters Patent is hereby corrected as shown below:

In the Claims

In Column 5, Line 36, Claim 1, delete "interface:" and insert -- interface; --, therefor.

Signed and Sealed this
Twenty-seventh Day of August, 2019

Andrei Iancu
*Director of the United States Patent and Trademark Office*